(12) United States Patent
Zhang et al.

(10) Patent No.: US 8,597,637 B1
(45) Date of Patent: Dec. 3, 2013

(54) BREAST CANCER THERAPY USING AN ENGINEERED RESPIRATORY SYNCYTIAL VIRUS

(76) Inventors: Weidong Zhang, Tampa, FL (US); Lixian Jiang, Wesley Chapel, FL (US); Calvin Cao, Tampa, FL (US)

( * ) Notice: Subject to any disclaimer, the term of this patent is extended or adjusted under 35 U.S.C. 154(b) by 224 days.

(21) Appl. No.: 12/800,585

(22) Filed: May 18, 2010

(51) Int. Cl.
*A01N 63/00* (2006.01)
*A01N 65/00* (2009.01)
*A61K 48/00* (2006.01)
*C12Q 1/70* (2006.01)

(52) U.S. Cl.
USPC ............... 424/93.2; 424/93.1; 435/5

(58) Field of Classification Search
None
See application file for complete search history.

(56) References Cited

U.S. PATENT DOCUMENTS

| | | |
|---|---|---|
| 2008/0180039 A1 | 7/2008 | Masuko |
| 2008/0279892 A1 | 11/2008 | Jin |
| 2010/0303839 A1* | 12/2010 | Bose et al. ................. 424/184.1 |

OTHER PUBLICATIONS

Zhou, et al. (Apr. 3, 2007) "Enhanced NF[kappa]B and AP-1 transcriptional activity associated with antiestrogen resistant breast cancer", BMC Cancer, 7(59): pp. 1-15.*
Spann, et al. (2004) "Suppression of the Induction of Alpha, Beta, and Gamma Interferons by the NS1 and NS2 Proteins of Human Respiratory Syncytial Virus in Human Epithelial Cells and Macrophages" Journal of Virology, 78(8): 4363-69.*
W. Zhang. Flow cytometry log record of apoptosis tested in lung cancer using cell line A549 after treated with siNS1 (NS1 gene muted with siRNA), work was done before May 2004.
W. Zhang, et al. Inhibition of respiratory syncytial virus infection with intranasal siRNA nanoparticles targeting the viral NS1 gene. Nat Med. Jan. 2005;11(1):56-62.
W. Zhang. Experimental log record of NS1 dificient RSV kill human lung cancer cells in nude mice. Work was done before Oct. 2007.
W. Zhang. Lab summary of "NS1-deficient RSV kills cancer cells in vitro and in vivo" Dated on Nov. 2008.
W. Zhang, et al, Email communication with Dr. Gary Hellermann regarding his Florida biomed grant (Lung cancer therapy mediated by a novel oncolytic RSV . . . , Jan. 2009).
W. Zhang. Confirmation letter from NIH indicates that they received his grant "Targeting lung cancer with an oncolytic engineered respiratory syncytial virus" (Jun. 2009).
W. Zhang. His NIH grant proposal package ("Targeting lung cancer with an oncolytic engineered respiratory syncytial virus") downloaded from NIH eRA commons. Jun. 2009.
U.S. Appl. No. 12/925,886, Wediong Zhang, Lixian Jiang, Calvin Cao, Lung cancer therapy using an engineered respiratory syncytial virus, filed Nov. 2, 2010, par. [0008], [0009], [0010], [0026].
Munir et al. (2008) Journal of Virology, 82, 8790-8796.
Iran et al. (2007) Virology, 368, 73-82.
Jin et al. (2000) Virology, 273, 210-218.

* cited by examiner

*Primary Examiner* — Robert M Kelly

(57) ABSTRACT

The invention discloses an engineered oncolytic respiratory syncytial virus (RSV), NS1 gene deficient RSV, and its usage to treat breast cancer by killing cancer cells with in vitro and in vivo evidences.

6 Claims, 11 Drawing Sheets

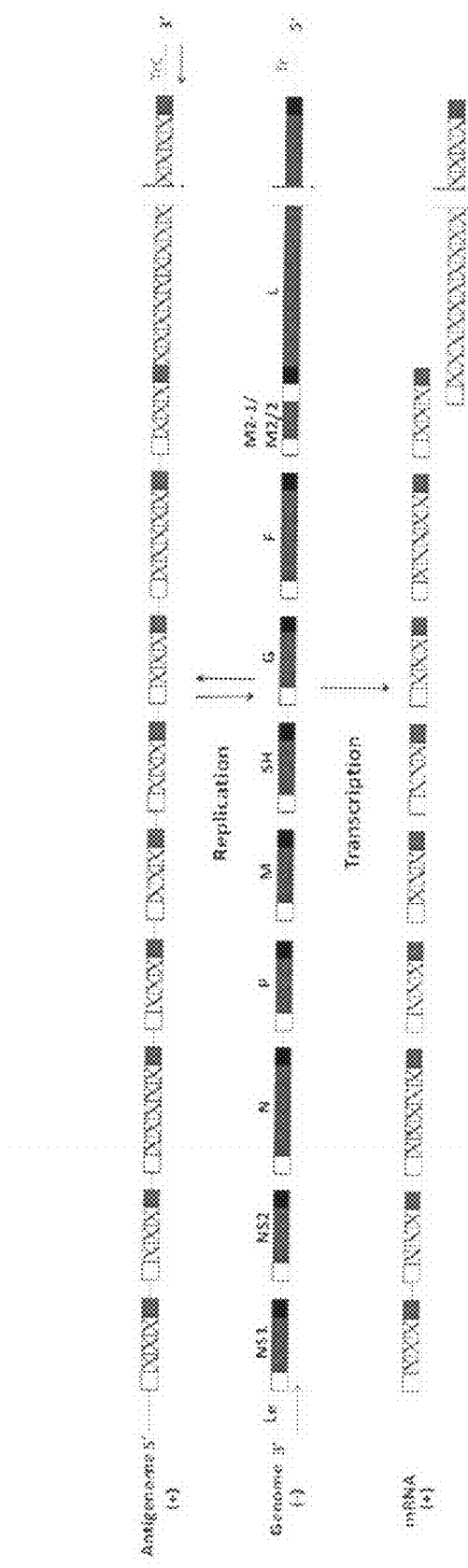

Fig. 1 Diagram of the RSV genome and its transcription and replication products. The virus genes are depicted grey rectangles. The L gene, which comprises almost half of the genomes, has been truncated. The GS and GE signals are shown as white and black boxes, respectively. The encoded anti-genome and mRNAs are indicated by hatched rectangles. Arrows indicate the location of the promoters.

BREAST CANCER THERAPY USING AN ENGINEERED RESPIRATORY SYNCYTIAL VIRUS

FIELD OF THE INVENTION

The invention is within the scope of oncolytic virotherapy. We engineered respiratory syncytial virus (RSV) by deleting NS1 gene, and found that the NS1 gene deficient RSV (ΔNS1 RSV) can kill breast cancer cells, but not normal human cells.

BACKGROUND OF THE INVENTION

Breast cancer: Breast cancer is the most commonly cancer among women, with more than one million new cases identified worldwide each year [1]. An estimated 192,370 patients were newly diagnosed with breast cancer in the United States in 2009, and about 40,170 died of the disease [2]. Approximately 24% to 30% of women who have no lymph-node involvement at the time of diagnosis will relapse; the relapse rate for node-positive women is between 50%-60%[3]. The 5-year survival rates for those diagnosed with regional and metastatic disease are 80% and 26%, respectively[3]. Therefore, a safe and effective treatment remains a critical need.

Oncolytic virotherapy. Oncolytic virotherapy is a novel strategy using viruses, either naturally occurring or genetically modified, to selectively target and destroy tumor cells whilst leaving surrounding non-malignant cells unharmed [4]. The destruction of cancer cells occurs either through direct lytic rupture by multi-cycle viral replication or the subsequent induction of apoptosis[5] and successful application of virotherapy requires preferential and efficient amplification of the virus to lyse cancer cells. NS1 gene deficient RSV (ΔNS1 RSV) functions as an oncolytic virus against breast cancer.

RSV biology. RSV belongs to the family Paramyxoviridae, subfamily Pneumovirinae, genus Pneumovirus. The viral RNA is approximately 15 kb in size and is flanked by a leader region at the 3' extremity of the genome and by a trailer region at the 5' extremity (FIG. 1). The viral genome contains individual genes for ten viral proteins [6]. The NS1 gene, unique to members of the genus Pneumovirus [7], is promoter-proximally located at the 3' end of the viral genome and its mRNA is the most abundant of the RSV transcripts in a linear start-stop-restart mode [8]. NS1 protein is referred to as nonstructural since it has not been detected in RSV particles. NS1 is exclusively found in RSV-infected cells. Our group, along with others, has found that NS1 can counter the type I IFN signaling during RSV infection [9, 10], implying that NS1 plays a direct role in inhibiting the host's innate immune response.

RSV can be rendered nonpathogenic by mutating the NS1 gene so that it no longer inhibits IFN release, which attenuates viral infection in normal cells. However, these nonpathogenic RSV, ΔNS1 RSV, are still oncolytic because tumor cells are defective in their ability to produce and respond to IFN and, therefore, efficiently support the propagation of ΔNS1 RSV.

SUMMARY

This invention discloses a NS1 gene deficient RSV (ΔNS1 RSV), which could be utilize to kill breast cancer cells, but not normal human cells. In one embodiment, the gene NS1 is deleted by the removal of 122 to 630 nt in the antigenomic cDNA using reverse genetics approach, resulting in the joining of the upstream nontranslated region of NS1 to the translational initiation codon of NS2. The ΔNS1 RSV was recovered through co-transfecting Vero cells with the NS1-deficient RSV cDNA and expressional plasmids encoding N, P, M2-1 and L. The RSV NS1 protein functions as a type-I-IFN antagonist, ΔNS1 RSV virotherapy produces more type-I-IFN, which prevents virus from replication in normal cells and also induces antitumor effects In another embodiment, the engineered virus could be any other virus having a similar strategy to delete NS1 gene, which functions as a gene encoding the related protein as a type-I-IFN antagonist.

In another embodiment, the ΔNS1 RSV can be applied to cancer spot by direct injection. Or the ΔNS1 RSV can be delivered to cancer spot through blood transfusion.

BRIEF DESCRIPTION OF THE FIGURES

FIG. 1. Diagram of the RSV genome and its transcription and replication products.

FIG. 2C. Viral titers as measured by plaque assay at 24 h after infection. Standard deviations from three independent experiments are shown by the error bars.

Table 1. Cytopathic effect (CPE) test showing ΔNS1 RSV selectively kills human breast cancer cells

DETAILED DESCRIPTION OF THE INVENTION

The respiratory syncytial virus (RSV) was used in this study. The NS1 gene was deleted by the removal of 122 to 630 nt in the antigenomic cDNA using reverse genetics approach, resulting in the joining of the upstream nontranslated region of NS1 to the translational initiation codon of NS2. The ΔNS1 RSV was recovered through cotransfecting Vero cells with the NS1-deficient viral cDNA clone and expressional plasmids encoding N, P, M2-1 and L. Alternatively, the engineered virus could be any other viruses with the deletion of similar NS1 gene.

Figure 2A:
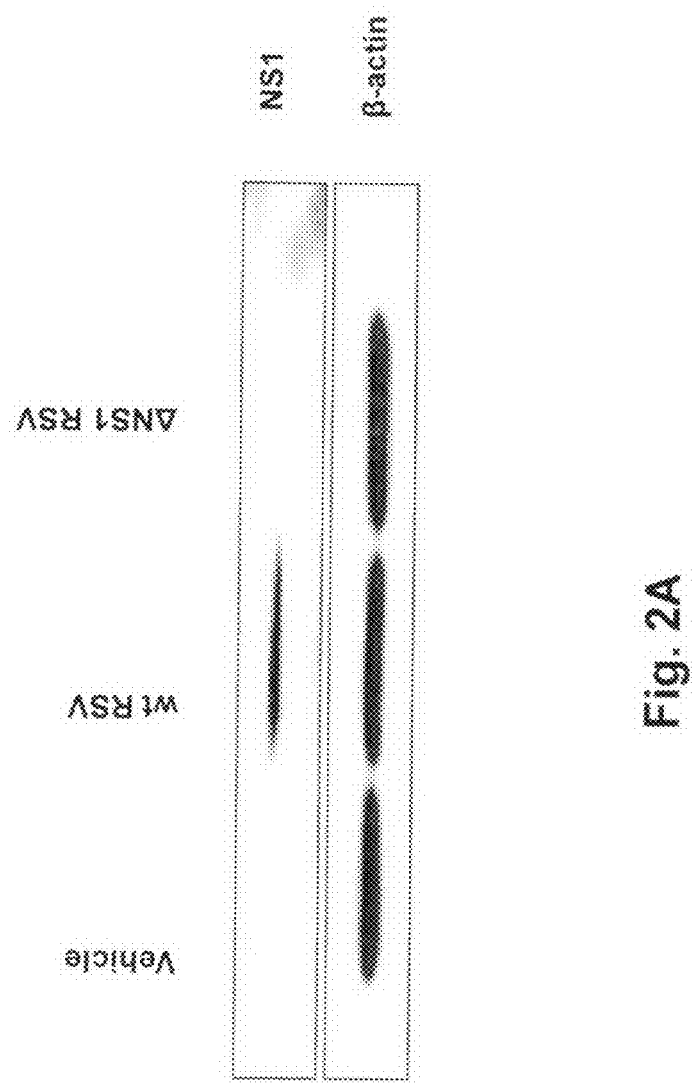
FIG. 2A. Verify viral NS1 protein by immunoblotting using anti-NS1 antibodies.

To identify whether ΔNS1 RSV lacks NS1 gene, we infected Vero cells (IFN-f3 gene deficient cells) with wt RSV and ΔNS1 RSV (MOI=5), NS1 protein were tested using NS1 specific antibodies by immunoblotting. As shown in FIG. 2A, NS1 protein was only visualized in wt RSV-infected Vero cells, not ΔNS1 RSV-infected cells, indicating that ΔNS1 RSV lacks NS1 gene.

Figure 2B:
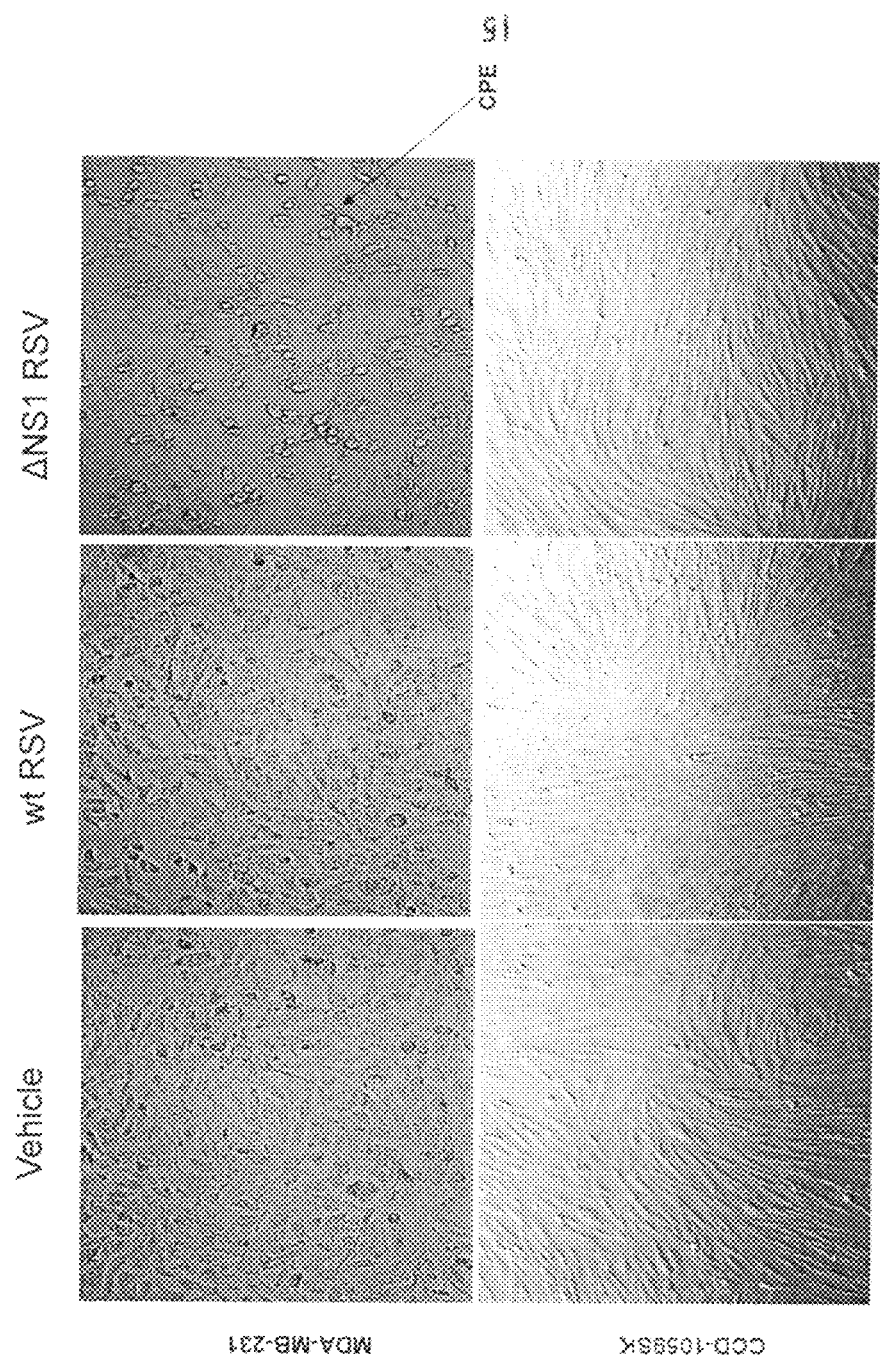
FIG. 2B. Morphology of virus-infected MDA-MB-231 and CCD-1059 SK cells 24 h post-infection.
Figure 2C:
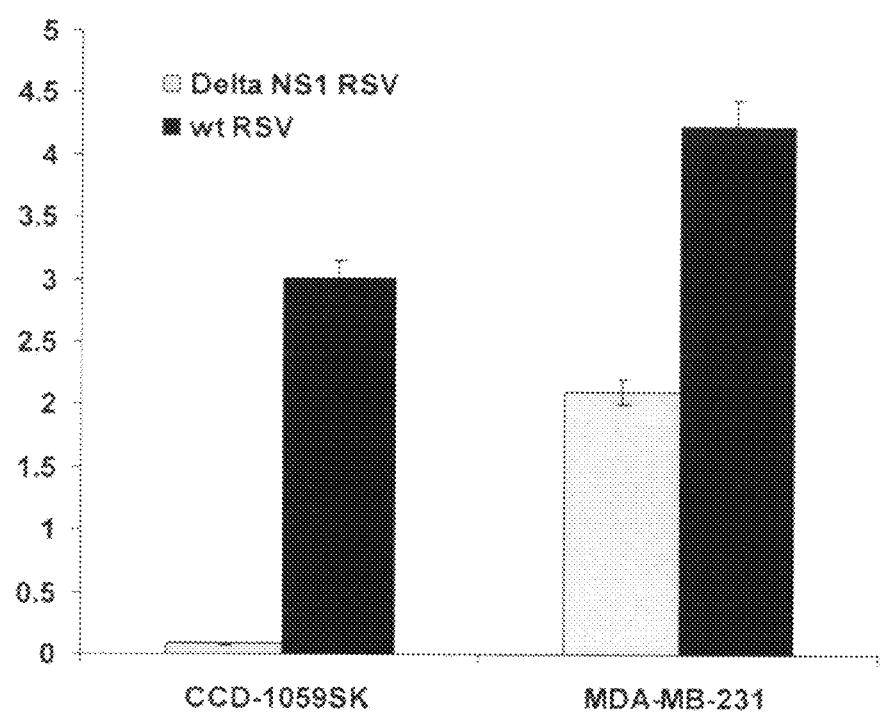
Figure 2D:
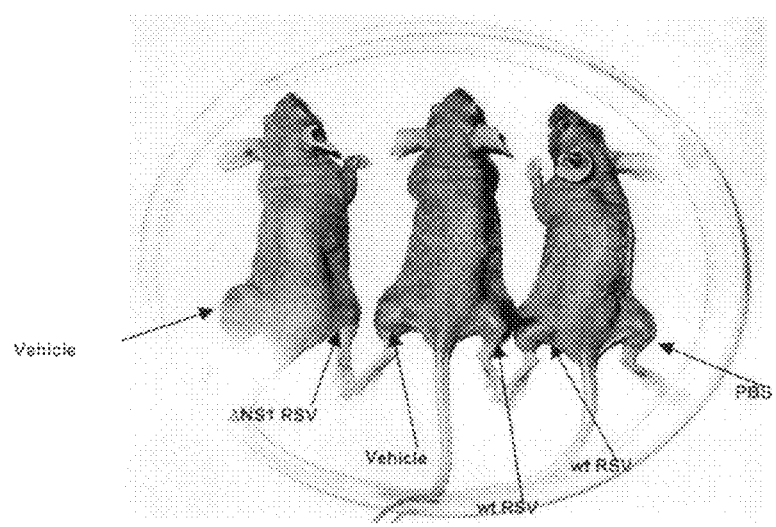
FIG. 2D. In vivo test virotherapy. Subcutaneous MDA-MB-231 tumors were implanted in BALB/c nude mice and the size was photographed. Control mice received equal volume of vehicle or PBS. Tumor sizes were measured at the end of treatment. Each data point represents a mean of 6 tumors measurements plus or minus the standard deviation.

ΔNS1 RSV preferentially kills breast cells both in vitro and in vivo. MDA-MB231 breast cancer cells and normal CCD-1059SK (Human normal breast fibroblast) were cultured in as indicated by ATCC (American Type Culture Collection) instruction, and then infected with wt and ΔNS1 RSV (MOI=5). Changes in cell morphology were observed and viral replication was measured. FIG. 2B shows that ΔNS1 RSV selectively induces cytopathic effect (CPE) in MDA-MB-231 breast cancer cells, and that ΔNS1 RSV has a higher viral titer in this tumor cells than in CCD-1059SK cells 24 h post-infection (FIG. 2C), suggesting that MDA-MB-231 cells efficiently support the propagation of ΔNS1 RSV. To test if ΔNS1 RSV also kills other breast cancer cell lines, we infected breast cancer cell lines T-47D and MCF-7 with ΔNS1 RSV (MOI=5). CPEs were observed 48 h post-infection (Table 1), indicating ΔNS1 RSV specifically kills breast cancer cells.

TABLE 1

ΔNS1 RSV selectively kills human breast cancer cells

| | CPE (hr post-infection) | | | |
| --- | --- | --- | --- | --- |
| | 24 hr | | 48 hr | |
| Virus (MOI = 10)<br>Cells | ΔNSI RSV | wt RSV | ΔNS1 RSV | wt RSV |
| CCD-1059Sk (Human normal breast fibroblast) | − | − | + | − |
| MDA-MB-231 (Breast, adenocarcinoma, p53−) | ++++ | − | + | − |
| T-47D (Breast, ductal carcinoma, p53−) | ++ | − | + | − |
| MCF7 (Breast, adenocarcinoma, p53+) | ++ | − | + | − |

Note:
−: no CPE; ++: CPE ≤ 50%; ++++: CPE ≥ 75%

Figure 2E:
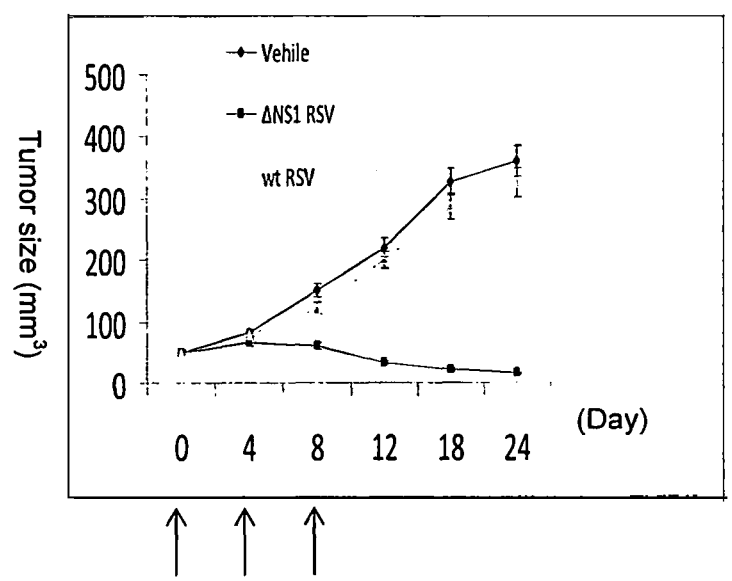
FIG. 2E. The tumor sizes were measured, and virotherapy is indicated by arrows below the x-axis. Control mice received equal volume of vehicle or PBS. Tumor sizes were measured at the end of treatment. Each data point represents a mean of 6 tumors measurements plus or minus the standard deviation.
Figure 2F:
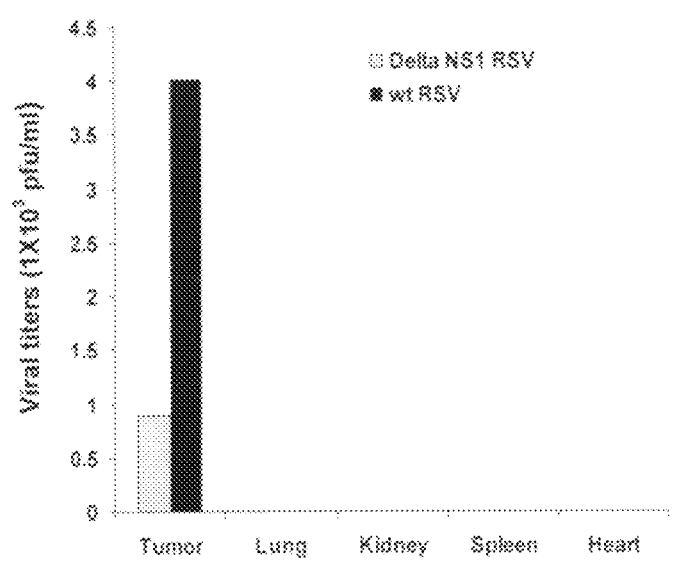
FIG. 2F. Viral titers were measured in different tissue homogenates from the same animal to test virus safety after three days injection of viruses.
Figure 2G:
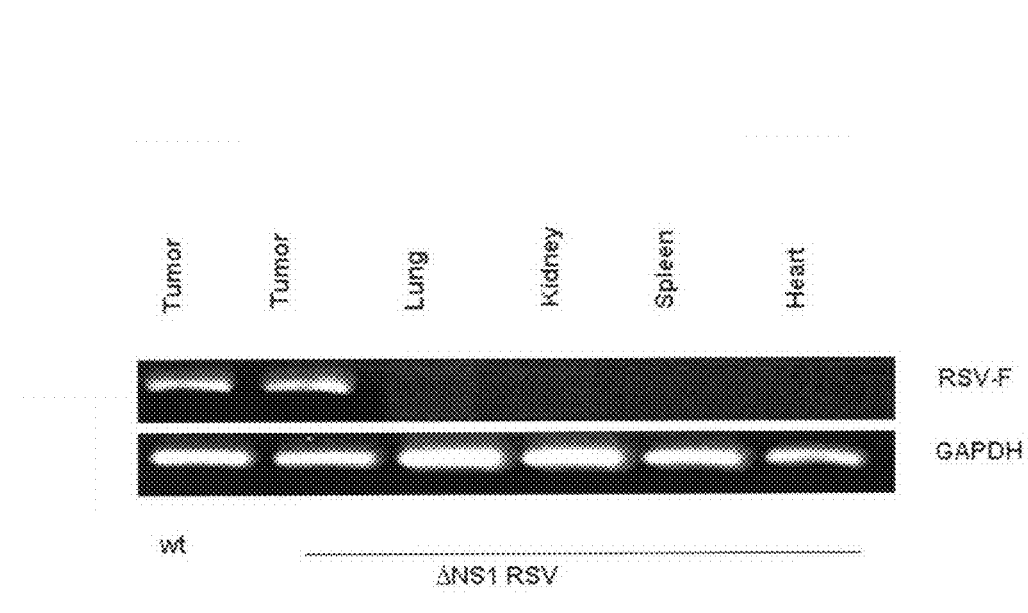
FIG. 2G. Viral F gene expression[9] was analyzed by RT-PCR to test virus safety in different organ from the same individual after three days virotherapy.

To determine whether ΔNS1 RSV infection induces tumor growth regression in vivo, MDA-MB-231 breast cancer cells were injected s.c. into the left and right flanks of 4-6 weeks old nude BALB/c mice (n=6 per group) and the resulting tumors were allowed to develop. Viruses (1×10$^{10}$ pfu/ml) were locally injected into the tumors three times and the sizes of the tumors were measured using digital calipers. FIG. 2C, D show that ΔNS1 RSV infection caused regression in tumor growth versus controls. To test the safety of locally administered viruses, the virus titer in various organs of infected mice was determined by plaque assay and RT-PCR assay. As shown in FIG. 2E, F, the viruses specifically localize to tumors.

Figure 3A:
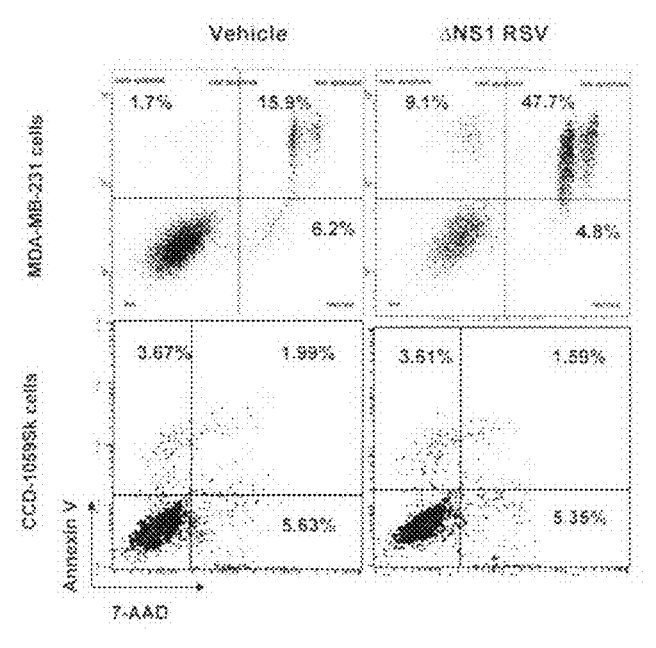
Figure 3:
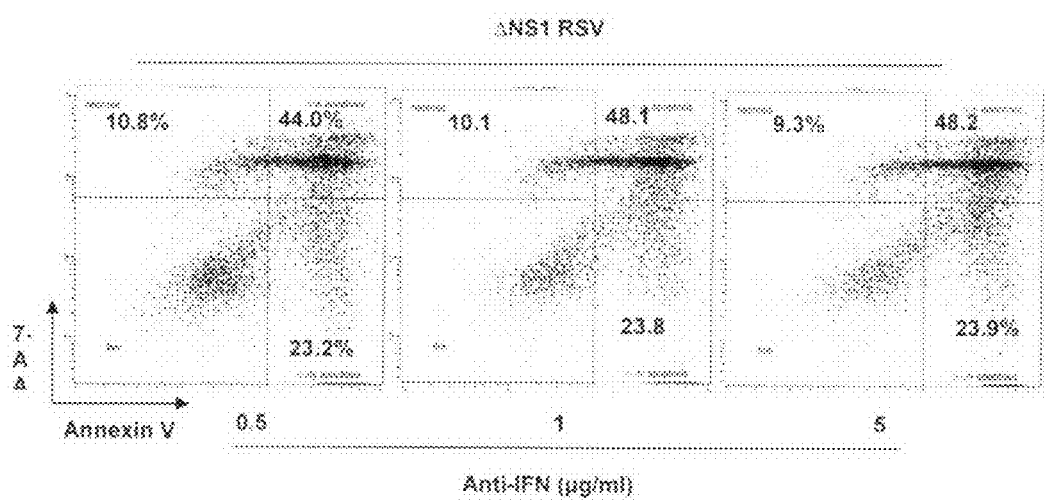
FIG. 3A. MDA-MB-231 and CCD-1059 SK cells were infected with indicated viruses (MOI=5), and collected at 20 and 48 hr post-infection for apoptosis analysis by annexin V-binding and PI uptake assay.
FIG. 3B. MDA-MB-231 cells were infected with viruses (MOM) and neutralizing Abs against IFN-β (ND50 is ~0.05-0.2 µg/ml PBL Interferon Source) were added 15 min post-infection, and apoptosis were measured by annexin V-binding and PI uptake assay.
FIG. 3C. Vero cells were infected with indicated viruses (MOI=5) and apoptosis was measured by annexin V-binding and PI uptake assay.

ΔNS1 RSV infection induces apoptosis in tumor cells, but not in normal human breast fibroblast CCD-1059SK cells. To test the differential effect of ΔNS1 RSV infection on apoptosis, MDA-MB-231 tumor cells and normal CCD-1059 SK cells were infected with the indicated viruses (MOI=5) and apoptosis was measured by the annexin V binding assay. FIG. 3A shows that ΔNS1 RSV selectively induces apoptosis in tumor cells, compared to the cell spontaneous apoptosis shown in control.

Figure 3C:
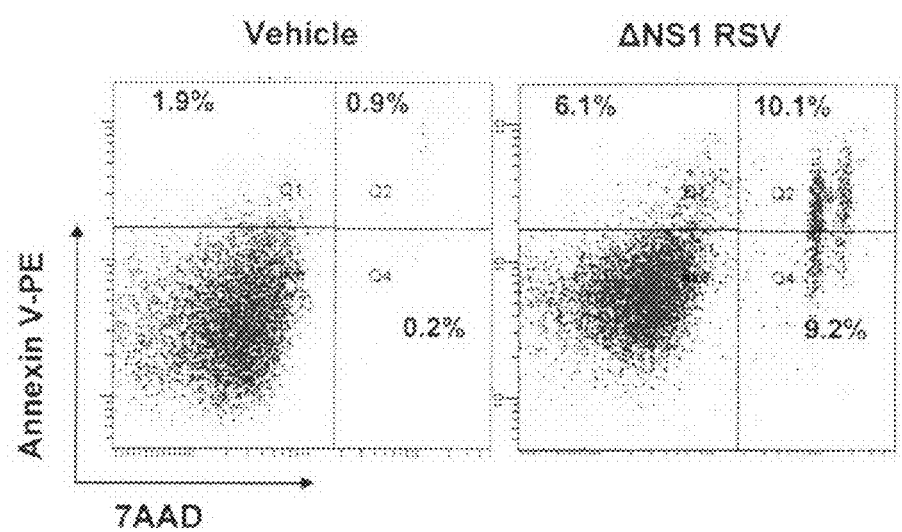

Knockdown of the RSV NS1 gene allows the production of more IFN-f3 in A549 cells [9]. To further study the involvement of IFN-f3 in virus-induced apoptosis in breast cancer cells, neutralizing Abs against IFN-f3 were used to block IFN activity, but failed to attenuate apoptosis in breast cancer cells induced by viral infection (FIG. 3B). To confirm this finding, we infected Vero cells (IFN-f3 gene deficient cells) with ΔNS1 RSV, apoptosis was measured by the annexin V binding assay. FIG. 3C shows that ΔNS1 RSV still induces apoptosis in Vero cells, compared to the control, suggesting that IFN may not be involved in virus-induced apoptosis.

REFERENCES

1. Parkin, D. M., et al., *Global cancer statistics*, 2002. CA Cancer J Clin, 2005. 55(2): p. 74-108.
2. Jemal, A., et al., *Cancer statistics*, 2009. CA Cancer J Clin, 2009. 59(4): p. 225-49.
3. Donato, B. M., et al., *Treatment patterns in patients with advanced breast cancer who were exposed to an anthracycline, a taxane, and capecitabine: a descriptive report*. Clin Ther. 32(3): p. 546-54.
4. Parato, K. A., et al., *Recent progress in the battle between oncolytic viruses and tumours*. Nat Rev Cancer, 2005. 5(12): p. 965-76.
5. Berry, L. J., et al., *Potent oncolytic activity of human enteroviruses against human prostate cancer*. Prostate, 2008. 68(6): p. 577-87.
6. Collins, P. L., Y. T. Huang, and G. W. Wertz, *Identification of a tenth mRNA of respiratory syncytial virus and assignment of polypeptides to the 10 viral genes*. J Virol, 1984. 49(2): p. 572-8.
7. Hacking, D. and J. Hull, *Respiratory syncytial virus—viral biology and the host response*. J Infect, 2002. 45(1): p. 18-24.
8. Tran, K. C., P. L. Collins, and M. N. Teng, *Effects of altering the transcription termination signals of respiratory syncytial virus on viral gene expression and growth in vitro and in vivo*. J Virol, 2004. 78(2): p. 692-9.
9. Zhang, W., et al., *Inhibition of respiratory syncytial virus infection with intranasal siRNA nanoparticles targeting the viral NS1 gene*. Nat Med, 2005. 11(1): p. 56-62.
10. Spann, K. M., et al., *Suppression of the induction of alpha, beta, and lambda interferons by the NS1 and NS2 proteins of human respiratory syncytial virus in human epithelial cells and macrophages [corrected]*. J Virol, 2004. 78(8): p. 4363-9.

The invention claimed is:
1. A method to treat breast cancer in a patient in need thereof, comprising:
   1) suspending an engineered oncolytic respiratory syncytial virus (RSV) with the NS1 gene deleted in saline or medium, and
   2) injecting the RSV suspension into the cancerous tissue, wherein the RSV infects and causes oncolysis to thereby treat the patient.

2. The method of claim 1, wherein the RSV is suspended in saline.

3. The method of claim 1, wherein the RSV is suspended in medium.

4. A method to treat breast cancer in a patient in need thereof comprising:
   1) suspending an engineered oncolytic respiratory syncytial virus with the NS1 gene deleted, and further comprising the viral NS2, N, M, SH, G, F, M2-1, P, and L genes, in saline or medium, and 2) injecting the engineered RSV suspension into cancerous tissue, wherein the RSV infects and causes oncolysis to thereby treat the patient.

5. The method of claim 4, wherein the engineered RSV is suspended in saline.

6. The method of claim 4, wherein the engineered RSV is suspended in medium.

* * * * *